US012690795B2

(12) United States Patent
Zhang et al.

(10) Patent No.: US 12,690,795 B2
(45) Date of Patent: Jul. 28, 2026

(54) REINFORCEMENT LEARNING BASED ADAPTIVE STATE OBSERVATION FOR BRAIN- MACHINE INTERFACE

(71) Applicant: The Hong Kong University of Science and Technology, Hong Kong (CN)

(72) Inventors: Xiang Zhang, Hong Kong (CN); Zhiwei Song, Hong Kong (CN); Yiwen Wang, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 1083 days.

(21) Appl. No.: 17/664,888

(22) Filed: May 25, 2022

(65) Prior Publication Data

US 2023/0010664 A1 Jan. 12, 2023

Related U.S. Application Data

(60) Provisional application No. 63/220,994, filed on Jul. 12, 2021.

(51) Int. Cl.
*A61B 5/31* (2021.01)
*A61B 5/11* (2006.01)
(Continued)

(52) U.S. Cl.
CPC .............. *A61B 5/31* (2021.01); *A61B 5/1104* (2013.01); *A61B 5/372* (2021.01); *A61F 2/72* (2013.01); *G06F 3/015* (2013.01); *G06N 3/048* (2023.01)

(58) Field of Classification Search
None
See application file for complete search history.

(56) References Cited

U.S. PATENT DOCUMENTS

| | | |
|---|---|---|
| 9,050,200 B2 | 6/2015 | Digiovanna et al. |
| 10,439,836 B2 | 10/2019 | Rosenberg et al. |

(Continued)

FOREIGN PATENT DOCUMENTS

| | | |
|---|---|---|
| CN | 107102644 A | 8/2017 |
| WO | 2014025765 A2 | 2/2014 |

OTHER PUBLICATIONS

"Bayesian Population Decoding of Motor Cortical Activity Using a Kalman Filter," Neural Computation, Jan. 2006, 18(1):80-118, Wu et al; Wu. (Year: 2006).*
"Bayesian Population Decoding of Motor Cortical Activity Using a Kalman Filter," Neural Computation, Jan. 2006, 18(2):80-228, Wu et al; Wu. (Year: 2006).*

(Continued)

*Primary Examiner* — Michael J Huntley
*Assistant Examiner* — Paul J Breene
(74) *Attorney, Agent, or Firm* — S&F/WEHRW

(57) ABSTRACT

A reinforcement learning (RL) based adaptive state observation model usable for implementing a brain machine interface (BMI) is proposed for decoding a brain signal to determine a movement action and controlling a machine to perform the movement action. In the model, the brain signal is processed by a neural network (NN) for applying a nonlinear mapping defined by NN weights to the brain signal to thereby yield a transformed brain signal. The NN learns the nonlinear mapping by RL, allowing the weights to be adaptively and continuously updated to follow nonlinearity and non-stationarity of the brain signal. The transformed brain signal is processed by a Kalman filter (KF) to yield a control signal for controlling the machine to perform the movement action, thereby utilizing the KF to provide smooth generation of the control signal while blocking adverse influence of nonlinearity and non-stationarity of the brain signal to the KF.

20 Claims, 8 Drawing Sheets

(51) Int. Cl.

| | |
|---|---|
| *A61B 5/372* | (2021.01) |
| *A61F 2/72* | (2006.01) |
| *G06F 3/01* | (2006.01) |
| *G06N 3/048* | (2023.01) |

(56) References Cited

U.S. PATENT DOCUMENTS

| | | |
|---|---|---|
| 2012/0016435 A1 | 1/2012 | Rom |
| 2018/0260685 A1 | 9/2018 | Passot et al. |
| 2019/0025917 A1* | 1/2019 | Francis ................. A61B 5/375 |

OTHER PUBLICATIONS

"Non-invasive electroencephalographical (EEG) recording system in awake monkeys," Heliyon 6(2020), Nakamura et al; Nakamura. (Year: 2020).*

P. R. Roelfsema and A. Van Ooyen, "Attention-gated reinforcement learning of internal representations for classification," Neural computation, vol. 17, No. 10, pp. 2176-2214, 2005.

J. Digiovanna et al., "Coadaptive Brain-Machine Interface via Reinforcement Learning," IEEE Transactions on Bio-Medical Engineering, vol. 56, issue 1, pp. 54-64, Jan. 2009.

J. An et al., "Near Perfect Neural Critic from Motor Cortical Activity toward an Autonomously Updating Brain Machine Interface," Proceedings of Annual International Conference of the IEEE Engineering in Medicine and Biology Society, pp.73-76, Jul. 2018.

* cited by examiner

Equate the transformed brain signal to be a plurality of scores respectively associated with a plurality of candidate movement actions competing to be the movement action.

510

Compute the plurality of weights.

520

Update the NN with the computed plurality of weights.

530

413

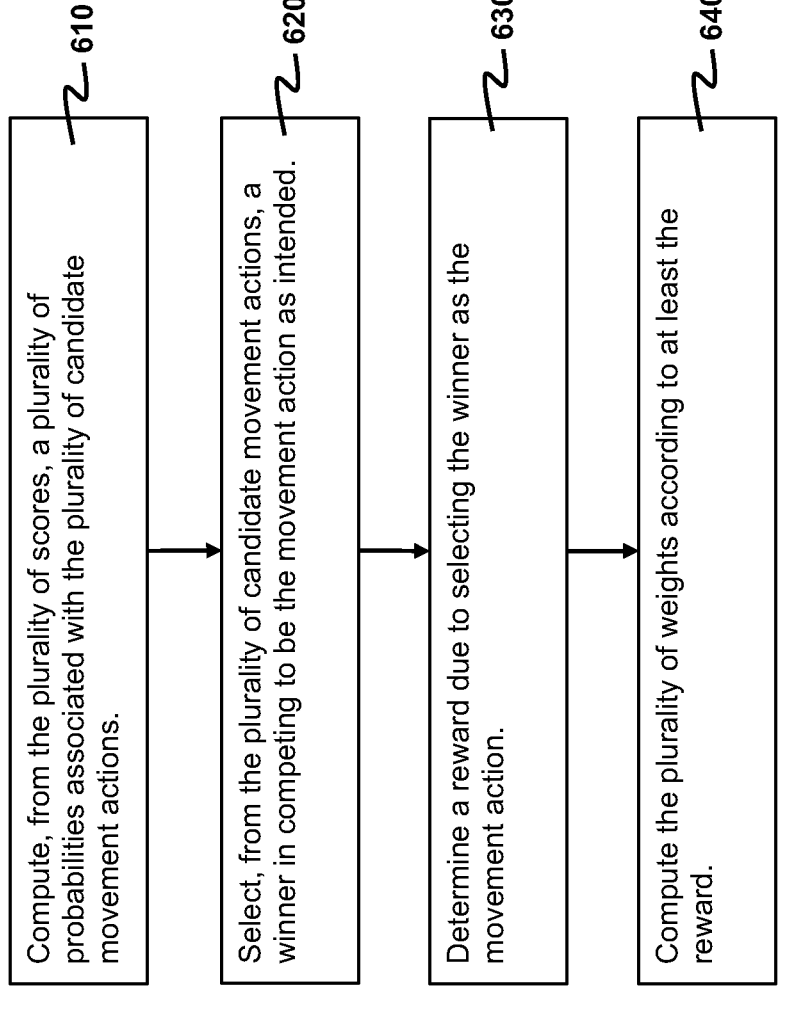

Compute, from the plurality of scores, a plurality of probabilities associated with the plurality of candidate movement actions. 〜610

Select, from the plurality of candidate movement actions, a winner in competing to be the movement action as intended. 〜620

Determine a reward due to selecting the winner as the movement action. 〜630

Compute the plurality of weights according to at least the reward. 〜640

REINFORCEMENT LEARNING BASED ADAPTIVE STATE OBSERVATION FOR BRAIN- MACHINE INTERFACE

CROSS-REFERENCE TO RELATED APPLICATIONS

This application claims the benefit of U.S. Provisional Patent Application No. 63/220,994 filed on Jul. 12, 2021, the disclosure of which is hereby incorporated by reference in its entirety.

LIST OF ABBREVIATIONS

AGREL Attention-gated reinforcement learning
BC Brain control
BMI Brain-machine interface
EEG Electroencephalography
fMRI Functional magnetic resonance imaging
KF Kalman filter
NN Neural network
MC Manual control
RL Reinforcement learning
SD Sprague Dawley

TECHNICAL FIELD

The present invention generally relates to a BMI for decoding a brain signal of a subject and controlling a machine to perform a movement action as intended by the brain signal. The BMI is usable for controlling movement of a neural prosthesis by a paralyzed patient's brain signal for restoring a motor function of the paralyzed patient. Furthermore, the present invention particularly relates to using a NN with RL and a KF to achieve smooth, adaptive state estimation of a continuous control process carried out in a nonlinear, non-stationary system as encountered in decoding the brain signal and generating a control signal to control the machine.

BACKGROUND

BMI establishes a direct communication pathway between a subject's brain and an external device. BMI collects noisy signals from neurons in the brain, and estimates a movement intention or an intended movement action from these signals. In one important area of practical applications, this estimated movement intention can be used to control a robot to perform mechanical actions so as to assist a motor disabled person. In another area of applications related to the gaming industry, the estimated movement intention may be used in controlling a virtual actor in a computer game.

Signal processing algorithms play a key role in BMI. As a commonly-used state-observation model, the KF has been adopted to decode the movement intents as the state from the high-dimensional observations formed by multiple neural firing activities, in which the movement state evolves over time as described by the linear state model of Kalman filtering, and the observation model reflects how the neuron firing tunes to movement in the presence of Gaussian noise. The implementation of the KF nicely considers the gradual change of the continuous brain state, and thus it is especially appropriate for the brain control task where the subject continuously adjusts the brain states to control an external robot. However, applying the state-observation model for BMI is challenging since a nervous system is nonlinear and nonstationary.

The state-observation model is a useful tool for accurate and stable state estimation of a system under consideration. The KF is a commonly used linear model. In Kalman filtering, a state transition function shows how the state is evolved. An observation function describes a linear mapping between the state and the observation in the presence of Gaussian noise. The KF exhibits an optimal performance for a stationary linear system. However, if the system is non-linear, Kalman filtering can only use a linear mapping to approximate the system. Thus, Kalman filtering might lead to poor performance. Moreover, in a nonstationary system, if the state-observation mapping becomes different from what is originally assumed in the training data, the KF cannot maintain a good performance with fixed parameters. A re-calibration session is required to collect the newest data. It is time-consuming.

RL is an alternative algorithm for adaptive state estimation. As an advantage, RL can non-linearly translate the observation to change the state. The translation is treated as an action in RL. If the action drives the state to be closer to the target, the observation-state mapping is reinforced by a reward signal; otherwise the mapping is punished. The reward signal can be generated continuously during usage so that the RL model can adaptively update its parameters to follow a non-stationary system. However, one of the drawbacks of RL is that it does not include the relationship between the previous state and the current state, making the state estimation not smooth. When a BMI is used for controlling a neural prosthesis in healthcare applications, having a non-smooth state estimate often leads to unnatural movement of the prosthesis.

There is a need in the art for an improved technique used in BMI for adaptive state estimation of a nonlinear nonstationary system while making the state estimation smooth.

SUMMARY

Mathematical equations referenced in this Summary can be found in Detailed Description.

A first aspect of the present invention is to provide a computer-implemented method for controlling a machine to perform a movement action determined by a brain signal of a subject.

In the method, the brain signal is processed by a NN for applying a nonlinear mapping defined by a plurality of weights of the NN to the brain signal to thereby yield a transformed brain signal. Furthermore, the plurality of weights is updated by a RL process such that the NN learns the nonlinear mapping by RL, allowing the nonlinear mapping to be adaptively and continuously updated to follow nonlinearity and non-stationarity of the brain signal. The transformed brain signal is then processed by a KF to yield a control signal for controlling the machine to perform the movement action. Advantageously, the KF is utilized to provide smooth generation of the control signal while blocking adverse influence of nonlinearity and non-stationarity of the brain signal to the KF in generating the control signal.

In the RL process, the transformed brain signal is equated to be a plurality of scores respectively associated with a plurality of candidate movement actions competing to be the movement action. An individual score of a respective candidate movement action is indicative to a probability that the respective candidate movement action is the movement action as intended by the brain signal. The plurality of weights is computed according to at least the plurality of scores. The NN is then updated with the computed plurality of weights for configuring the nonlinear mapping. Advantageously, the equating of the transformed brain signal to be the plurality of scores in computing the plurality of weights and updating the NN with the computed plurality of weights guides the nonlinear mapping to follow nonlinearity and non-stationarity of the brain signal while allowing RL to be applied to NN learning.

In certain embodiments, the computing of the plurality of weights according to at least the plurality of scores comprises: computing, from the plurality of scores, a plurality of probabilities associated with the plurality of candidate movement actions, wherein an individual probability associated with the respective candidate movement action is the probability that the respective candidate movement action is the movement action as intended by the brain signal; selecting, from the plurality of candidate movement actions, a winner in competing to be the movement action as intended according to the plurality of probabilities; determining a reward due to selecting the winner as the movement action according to whether or not the winner is actually the movement action as intended; and computing the plurality of weights according to at least the reward.

In certain embodiments, $P(\alpha_t=\text{k'})$, the probability that a k'th candidate movement action in the plurality of candidate movement actions is the movement action as intended by the brain signal, is computed by (10) where N is a total number of candidate movement actions in the plurality of candidate movement actions, $y_t=[y_1, \ldots, y_N]^T$ is the transformed brain signal with $y_k$ being a kth component of $y_t$, and $\alpha \geq 0$ is a controlling parameter.

In certain embodiments, the winner is selected to be a k*th candidate movement action from $P(\alpha_t=\text{k}^*)$ among all N probability values of $P(\alpha_t=\text{k'})$, k'=1, . . . , N.

In certain embodiments, $r_t$, the reward due to selecting the k*th candidate movement action as the movement action, is given by $r_t=1$ if the the k*th candidate movement action is the movement action as intended by the brain signal, and $r_t=0$ if not.

In certain embodiments, the NN is a three-layer NN comprising an input layer, a hidden layer and an output layer. The input layer has $D_z$ nodes for receiving the brain signal, and the brain signal also has $D_z$ components. The hidden layer has J hidden units. The output layer has N nodes for outputting the transformed brain signal. The transformed brain signal has N components. Furthermore, the plurality of weights is computed by (13) and (14), where: $w_{ij}$ is a weight from an ith node of the input layer to a jth hidden unit; $v_{jk*}$ is a weight from the jth hidden unit to a k*th node of the output layer; $\gamma$ is a learning rate; $\delta$ is an error function computed by $\delta=r_t-P(\alpha_t=\text{k}^*)$; $f(\delta)$ is an error expansive function given by (12); $z_{ti}$ is an ith component of $z_t$, the brain signal obtained at time step t; and $h_j$ is a value of the jth hidden unit, given by (8).

Exemplarily, the control signal is computed as $x_{t|t}$ given by (20) where: $x_{t|t}$ is a posterior estimation of a mean of a state x at time step t; $x_{t|t-1}$ is a prior estimation of the mean of the state x at time step t; and K is a Kalman gain given by (16), in which $P_{t|t}$ is a posterior estimation of the covariance of the state x at time step t, and R is a covariance matrix of a Gaussian noise term in $y_t$. The term $y_t$ is the transformed brain signal generated by the NN at time step t.

A second aspect of the present invention is to provide a system for capturing a brain signal of a subject and performing a movement action determined by the brain signal. The system comprises a sensing device, a machine and a computer. The sensing device is used for capturing the brain signal from the subject. The sensing device may be an EEG sensing device, a fMRI device, etc. The sensing device may even be a plurality of electrodes implanted in the brain of the subject. The machine is used for performing the movement action. The machine may be a prosthesis, a second computer configured to generate the movement action on a virtual object for virtual-reality applications, etc. The computer is configured to execute a computing process of processing the brain signal to determine the movement action and controlling the machine to perform the movement action according to any of the embodiments of the method as disclosed above.

A third aspect of the present invention is to provide a BMI apparatus for capturing a brain signal of a subject and controlling a machine to perform a movement action determined by the brain signal. The BMI apparatus comprises a sensing device and a computer. The sensing device is used for capturing the brain signal from the subject. The sensing device may be an EEG sensing device, a fMRI device, etc. The computer is configured to execute a computing process of processing the brain signal to determine the movement action and controlling the machine to perform the movement action according to any of the embodiments of the method as disclosed above.

Other aspects of the present disclosure are disclosed as illustrated by the embodiments hereinafter.

BRIEF DESCRIPTION OF THE DRAWINGS

FIG. 6 depicts certain embodiments of computing the plurality of weights.

DETAILED DESCRIPTION

Figure 1:
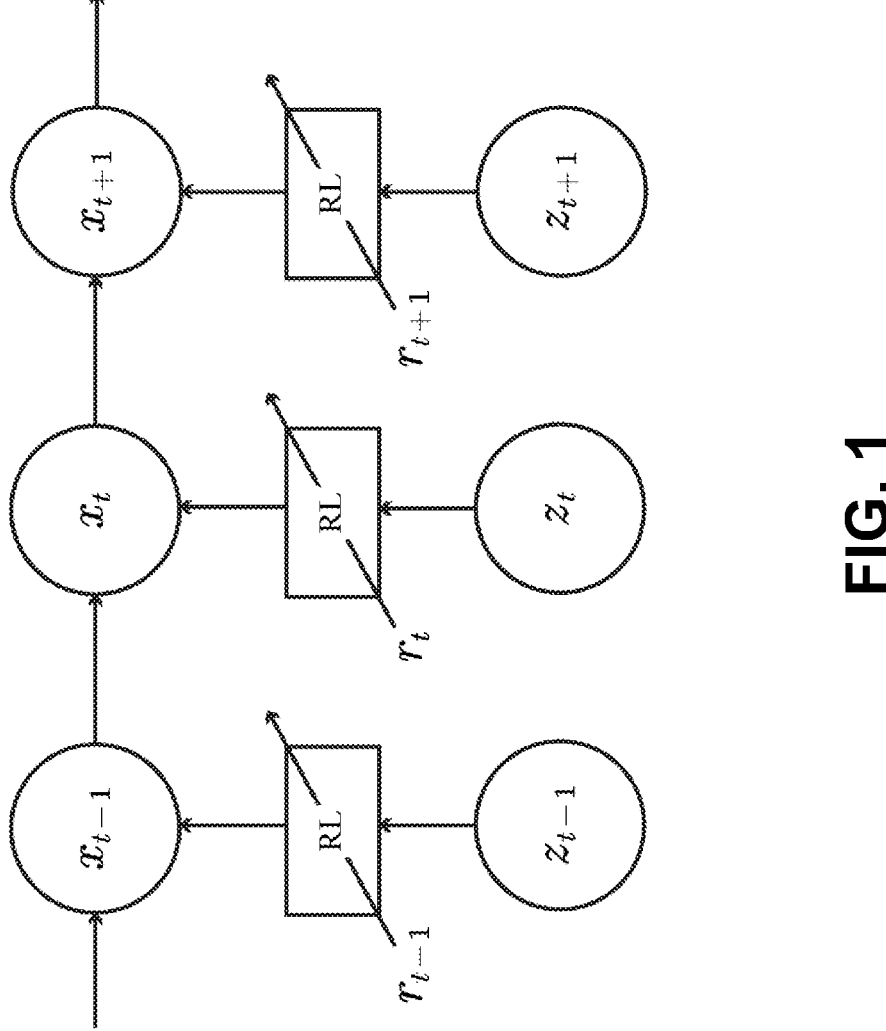
FIG. 1 depicts a schematic diagram of a disclosed algorithm for estimating a state of a RL-based adaptive state observation model as considered and disclosed in the present invention.

Unless otherwise stated, herein "a subject" is interpreted as a living individual that may be a human person or an animal.

As used herein, "a brain signal" is synonymous with a neural signal. Basically, a brain signal includes recordings of potentials that are presumably generated by mixing some underlying components of brain activity. Generally, the brain signal is a multidimensional signal. The brain signal may be obtained, for example, by EEG or by fMRI.

Unless otherwise stated, each of the following terms is understood to be an entity of any positive dimension: "a signal", "a state", "an observation" and "a noise". That is, the entity may be multidimensional with a plurality of components, or may be one-dimensional with one component. The present invention is related to decoding a brain signal. In the context of decoding the brain signal, such as an EEG signal, the brain signal is multidimensional in general.

Herein in the specification and appended claims, a signal, a state, an observation and a noise are each understood to be a vector quantity unless otherwise stated.

Herein in the specification and appended claims, "prior estimate" and "posterior estimate" are interpreted as technical terms used in Kalman filtering. In Kalman filtering, a prior estimate is a predicted estimate, and a posterior estimate is an updated estimate. "Prior estimation" and "posterior estimation" are similarly interpreted.

As used herein, "a movement action" is understood to be an action that causes a certain preselected object to move. Herein in the specification and claims, the preselected object encompasses may be a physical object, or a virtual object in the context of computer science. In one example, the physical object may be a neural prosthesis such that the action causes the prosthesis to set into physical motion and to move along a certain meaningful trajectory. In another example, the virtual object may be a computer-generated artificial arm presented to a computer-game player through a virtual-reality gaming station.

As used herein, the symbol '←' is an assignment operator meaning that the variable at the left hand side of the operator is assigned with a value computed by the expression shown on the right hand side of the operator.

Disclosed herein are method and system for decoding a brain signal of a subject to determine a movement action as intended by the subject and controlling a machine to perform the movement action. Advantageously, the disclosed method and system utilize a RL-based adaptive state observation model realized by combining RL and Kalman filtering. Before various embodiments of the present invention are elaborated, a theoretical development on the RL-based adaptive state observation model is provided.

A. Theoretical Development

The RL-based adaptive state observation model advantageously combines RL with a linear state transition model. A linear state transition function is used in the RL-based adaptive state observation model to provide a smooth estimation of the state evolution. At the same time, based on the current observation, RL is employed to nonlinearly refine the posterior state estimation. The refinement is considered as an action in RL and a reward signal is given to the action. During the continuous state estimation process, parameters used in RL are adaptively changed according to the reward signal. In this way, a timely updated nonlinear RL model to fine-tune the final state prediction is obtained, which can potentially follow the change of the state-observation mapping during usage in a nonlinear nonstationary system.

The linear state transition model employed in the disclosed RL-based adaptive state observation model is developed by considering Kalman filtering. A KF is a commonly-used linear state observation model. The detailed process of Kalman filtering is given as follows. Denote the state at the current time step t as a vector $x_t \in R^{D_x \times 1}$, where $D_x$ is the dimension of the state. The observation is denoted as $z_t \in R^{D_z \times 1}$, where $D_z$ is the dimension of the observation. The state and observation functions are given by $$x_t = Fx_{t-1} + q \tag{1}$$

and $$z_t = Hx_t + p \tag{2}$$

where: F is the state transition matrix; H represents the linear mapping from the state to the observation; and q and p are the noise of state transition and the noise of observation model, respectively. It is assumed that q and p are independent zero-mean Gaussian white noises with their covariance matrices being Q and R, respectively, i.e. q~N(0, Q) and p~N(0, R).

At the current time t, the posterior mean and covariance of the state from the previous time step are denoted as $x_{t-1|t-1}$ and $P_{t-1|t-1}$, respectively. From the state transition equation given by (1), one gets a prior update of the state as $$x_{t|t-1} = Fx_{t-1|t-1} \tag{3}$$

and $$P_{t|t-1} = FP_{t-1|t-1}F^T + Q, \tag{4}$$

where $x_{t|t-1}$ and $P_{t|t-1}$ represent the prior estimation of the mean and the prior estimation of the covariance, respectively, of the state at the current time.

After the prior estimation of the state is obtained, since the observation is also obtained at the same time t, it is required to have a posterior adjustment for the mean and covariance of the state. The computation steps are shown in the following equations:

$$K = P_{t|t-1}H^T(HP_{t|t-1}H^T + R)^{-1}, \tag{5}$$

$$x_{t|t} = x_{t|t-1} + K(z_t - Hx_{t|t-1}) \tag{6}$$

and $$P_{t|t} = (I - KH)P_{t|t-1}, \tag{7}$$

where: K is the Kalman gain, which is a coefficient determining the degree that one trusts the observation; and $x_{t|t}$ and $P_{t|t}$ are the posterior estimation of the mean and the posterior estimation of the covariance, respectively, of the current state.

The entire process of Kalman filtering for state estimation is summarized as follows. An initial condition is first set for the mean and covariance of the state, denoted as $x_0$ and $P_0$, respectively. At each time step, a prior update computed by (3) and (4) is first carried out. Then the current observation $z_t$ is employed to do a posterior update by (5)-(7). The mean value of the posterior state $x_{t|t}$ is the final output of the state from the KF.

In the present invention, AGREL is adopted as the RL scheme. For an explanation of the AGREL technique, see, for example, P. R. ROELFSEMA and A. VAN OOYEN, "Attention-Gated Reinforcement Learning of Internal Representations for Classification," *Neural Computation,* 17, 2176-2214 (2005). For illustration, the RL scheme employs a three-layer artificial NN to approximate any nonlinear mapping. In general, a NN having three or more layers may be used for approximating a nonlinear function. The input layer has $D_z$ nodes, and each node represents one component of the observation. The hidden layer has J nodes with the sigmoid activation function. Each of the J nodes of the hidden layer is referred to as a hidden unit. The output layer has N nodes, which represent the possible actions for the state. Each of the N nodes of the output layer is referred to as an output unit. The final action is selected probabilistically by the softmax policy based on the action value. If the action drives the state closer to the target, a reward $r_t=1$ is given to the algorithm, and $r_t=0$ otherwise. The reward signal is then used to update the weights that connect to the chosen action. A mathematical explanation is given as follows.

For the current observation $z_t$, the action selection process involves the following equations:

$$h_j = \frac{1}{1 + \exp\left(-\sum_{i=1}^{D_z} w_{ij}z_{ti}\right)}, \tag{8}$$

$$y_k = \sum_{j=1}^{J} v_{jk}h_j \tag{9}$$

and $$P(a_t = k') = \frac{\exp(\alpha y_{k'})}{\sum_{k=1}^{N} \exp(\alpha y_k)}. \tag{10}$$

The value of the hidden unit is calculated by (8), where $h_j$ is the output of the jth hidden unit; $w_{ij}$ is the weight from the ith input unit to the jth hidden unit; and $z_{ti}$ is the ith component of the current neural firing vector $z_t$. The action value is calculated by (9), where $y_k$ is the value of the kth output unit. The quantity $v_{jk}$ is the weight from the jth hidden unit to the kth output unit. The quantity $P(a_t=k')$ represents the probability of selecting the k'th action. The value $\alpha \geq 0$ is the parameter that controls the probability concentration of the softmax policy. If $\alpha$ is very large, the probability is concentrated more on large action values. If $\alpha$ is very small, the probability becomes similar for each action, making the RL scheme focus more on the exploration of different actions. Finally, an action is selected from the N possible actions. Denote k* as the index such that the k*th action is the selected action. Generally, k* is determined, according to some predefined rules, from $P(a_t=k^*)$ among the N probabilities computed by (10) for the N possible actions. One example of the predefined rules is provided as follows. During the training phase, k* is randomly determined as a Monte Carlo simulation outcome according to the N probabilities. During the testing phase, k* is a maximum-likelihood estimate such that $P(a_t=k^*)$ is largest among the N probabilities.

After the action is chosen, if the action moves the actuator towards the target, the instantaneous reward is given by $r_t=1$, otherwise $r_t=0$. The error signal $\delta$ and the error expansive function $f(\delta)$ are given by $$\delta = r_t - P(a_t = k^*) \tag{11}$$

and $$f(\delta) = \begin{cases} \frac{\delta}{1-\delta}, & \delta \geq 0, \\ -1, & \delta < 0. \end{cases} \tag{12}$$

The quantity $P(a_t=k^*)$ can be considered as the expectation of getting the reward by taking action k*. The error signal $\delta$ represents the difference between the actual reward and the expected reward. The error expansive function $f(\delta)$ is used to magnify the effect of an unexpected reward. When the action probability is low and it leads to a reward, $\delta$ is close to 1 and $f(\delta)$ takes a large value. The error expansive function $f(\delta)$ is then used in the weight update to increase the learning efficiency of the unexpected rewarding action, which mimics animal learning. The equations involved are given by $$v_{jk^*} \leftarrow v_{jk^*} + \gamma h_j f(\delta), j=1, \ldots, J, \tag{13}$$

and $$w_{ij} \leftarrow w_{ij} + \gamma z_{ti} h_j f(\delta) v_{jk^*}(1-h_j), i=1, \ldots, D_z \text{ and } j=1, \ldots, J, \tag{14}$$

where $\gamma$ is a learning rate, $w_{ij}$ is a weight from an ith node of the input layer to a jth hidden unit, and $v_{jk^*}$ is a weight from the jth hidden unit to a k*th node of the output layer. Note that only the weights connected to the selected action are updated.

The present invention, which achieves adaptive state estimation with a dynamic observation model via RL, is described as follows. In the present invention, the state transition function is the same as (1) so that the smooth state prediction is inherited from the linear state transition. Specifically, the observation function in (2) is modified as follows. Instead of using a linear mapping from the observation to the state, the AGREL technique is employed to nonlinearly generate a state from the observation, which is a nonlinearity denoted as $g_t(z_t)$. The modified observation function is given by $$g_t(z_t)=x_t+p \tag{15}$$

where p is the estimation noise of the RL model.

After the observation function is changed, the posterior update process is also changed. Then $z_t$ and H in (5)-(7) are equivalently replaced as $g_t(z_t)$ and the identity matrix I, respectively. The final update equations are shown as $$K=P_{t|t-1}(P_{t|t-1}+R)^{-1}, \tag{16}$$

$$x_{t|t}=x_{t|t-1}+K(g_t(z_t)-x_{t|t-1}) \tag{17}$$

and $$P_{t|t}=(I-K)P_{t|t-1}. \tag{18}$$

Note that since an artificial NN is used to generate the nonlinear mapping in the RL model, it follows that $$y_t=g_t(z_t) \tag{19}$$

where $y_t=[y_1, \ldots, y_N]^T$ is the output of the NN.

The algorithm disclosed above for estimating the state of the RL-based adaptive state observation model works as shown in FIG. 1, which is a schematic diagram depicting a structure of the disclosed algorithm. Initial values of $x_0$ and $P_0$ are first set. For each time step, the posterior motor state $x_{t|t}$ is calculated through (3), (4) and (16)-(18). After that, one can get the reward signal $r_t$ based on whether the state gets closer to the target. The reward signal is then used to update the parameters of AGREL as shown in (13) and (14). The non-linearity $g_t(\cdot)$ also changes accordingly. In this way, the disclosed algorithm has a potential to follow the change of the state-observation mapping during the control process in a nonlinear non-stationary system.

The advantages of the disclosed algorithm are summarized as follows. First, the disclosed algorithm combines the nonlinear RL model with a linear state transition model, leading to smooth and adaptive state estimation for a nonstationary system. Second, the present invention utilizes an advantage of RL of adjusting the parameters in an online fashion, which gets rid of the re-calibration session for a non-stationary system. It increases the time efficiency and improves the user experience during using the invention.

B. Experimental Verification

The algorithm disclosed above was tested on a BC task in BMI. BMI is a framework that can help paralyzed people restore their motor functions by translating their neural signals into the motion of external neuro-prostheses. In BMI, the state consists of one or more components selected from a neuro-prosthesis's position, velocity, etc. The observation is the neural signals that are extracted from the subject's brain. A human neural system is nonlinear in general, and it is also non-stationary due to neural plasticity.

Figure 2:
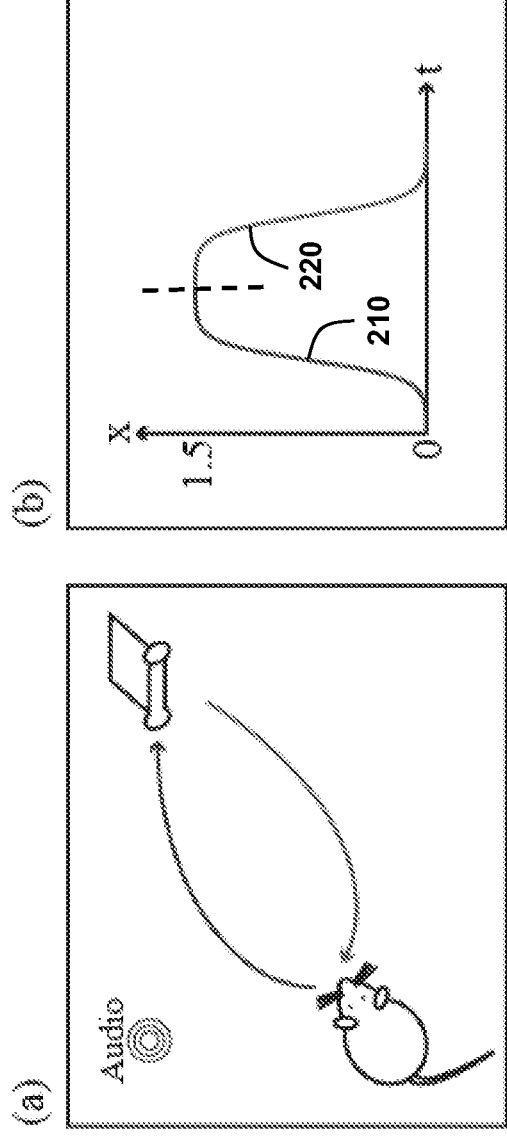
FIG. 2 illustrates a rat lever-pressing task used in an experiment for obtaining experimental results, where subplot (a) shows a physical movement trajectory of the rat in MC mode, and subplot (b) depicts a converted motor state in BC mode.

The disclosed algorithm was tested on a lever-pressing task for SD rats. The experimental paradigm is shown in FIG. 2. FIG. 2 depicts a rat lever-pressing task, where subplot (a) shows a physical movement trajectory of the rat in MC mode, and subplot (b) depicts a converted motor state in BC mode.

In subplot (a), the process of the MC training is shown. The rat needed to wait at the starting position. When it heard an audio cue (10 kHz, 0.9 s) indicating that the trial was started, the rat needed to get close to a lever, press and hold it for a period of time (0.5 s). Then this trial was successful. A second audio cue (10 kHz, 0.09 s) would be presented to the rat and the rat would come back to the starting position to get a water reward. If the rat did not hold the lever for enough time, or it did not press the lever within a time limit, this trial would be considered as a fail case and the rat could not get the reward. When one trial was finished, after a random inter-trial time was passed, another audio cue would be given to the rat to indicate that the next trial was started.

When the rat was doing the task, its neural signal was recorded simultaneously. The SD rat was implanted with two 16-channel microelectrodes, one in the primary motor cortex (M1) and another one in the medial prefrontal cortex (mPFC). Both were implanted in the left brain, which was contralateral to the rat's lever-pressing forearm in the task. During the experiment, the neural signals were recorded by Plexon (Plexon Inc, Dallas, Texas) with a 40 kHz sampling frequency. Then the neural signals were passed through a 4-pole Butterworth high pass filter (500 Hz). The spikes were detected by thresholding at $-4\sigma$ where $\sigma$ is the standard deviation of the signal amplitude. We counted the spikes within a 100 ms time non-overlapping window and we concatenated 7 windows of historical spikes, which makes the observation dimension $D_z=256$. The cue and movement events for the rats were recorded using a behavior system from Lafayette Instrument, USA. The event signals were synchronized with the neural signals from Plexon.

After the rat was proficient in doing the MC task, it was trained in a related BC task, which is shown in subplot (b) of FIG. 2. In the BC task, there was no physical lever for the rat to press. The rat's physical trajectory in doing the MC task was translated into a one-dimensional cursor state $x_t \in R^{D_x \times 1}$ ($D_x=1$). At the beginning of the trial, it was assumed that the cursor was around 0. When the rat approached the lever, the cursor rose from 0 to 1.5 as shown by a first part 210 of curve. During the holding period on the lever, the cursor was maintained at around 1.5. When the trial was successful and the rat came back to get the reward, the cursor went from 1.5 to 0 as shown by a second part 220 of curve. Based on the converted cursor trajectory (state) and the simultaneous spikes (observation), the parameters of the KF were trained. Then the rat began to brain-control the cursor purely using its neural signals. The details of the rat's BC training are given as follows. When the cursor stayed within the range (0, 0.75) for a pre-defined time, an audio cue (same as MC) would be presented to the rat, indicating that the trial started. The rat would try to move the cursor into the region (0.75, 1.5). If the cursor was located within the region for a given period of time (same as in MC), this trial was considered successful. The successful audio cue (same as MC) was given to the rat and the rat could get the water reward. If the cursor did not stay within (0.75, 1.5) for enough time, or it did not move into the region, this trial was considered as a fail case and the rat could not get the reward. After one trial was finished, it was unlike in the MC task where the next trial would start after a random time interval. To start the next trial in the BC task, the rat had to move the cursor to within (0, 0.75) and stay there for a pre-defined time period. Otherwise, the next trial would not be started.

The experiment collected 7 days of neural (observation) and trajectory (state) data when the rat was proficient in the BC task with the same KF parameters. Then the algorithm disclosed above was trained by the recorded data sequentially from day 1 to day 7. The disclosed algorithm was also tested with fixed parameters after day 1. As a reference, a linear KF was also tested. The experimental results are shown in FIGS. 3A-3C.

Figure 3A:
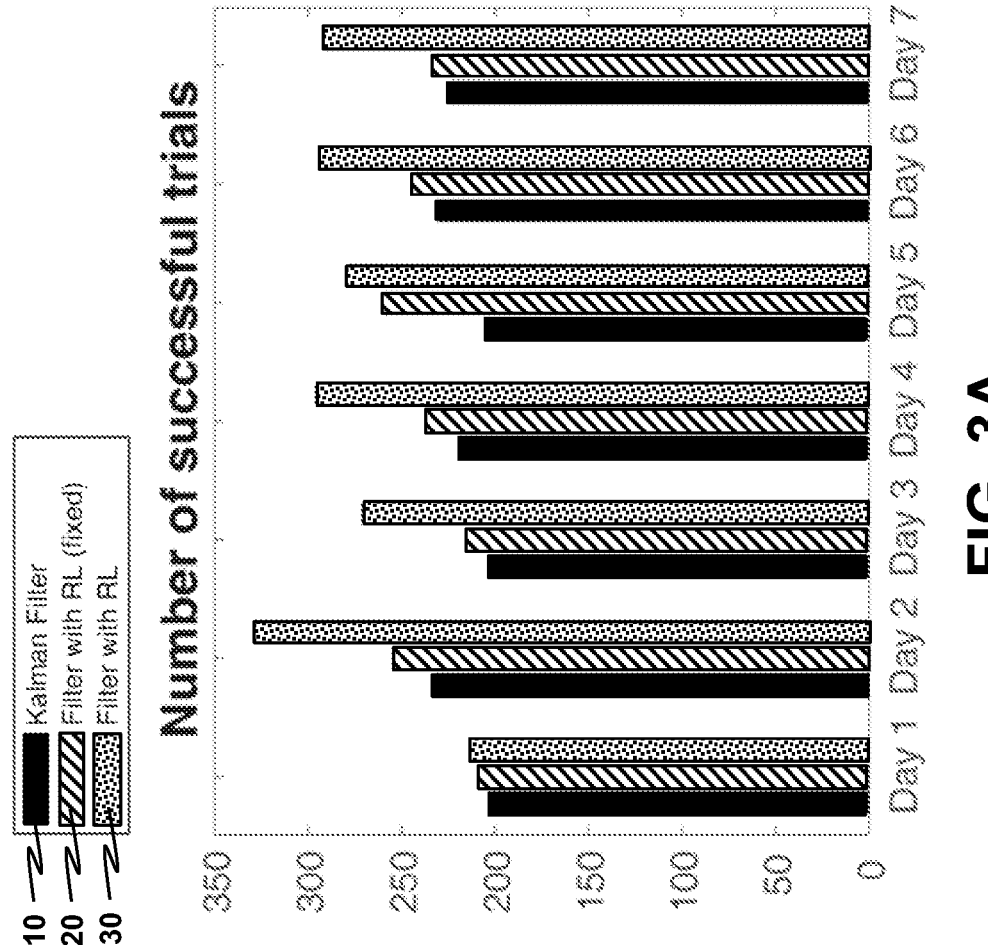
FIG. 3A plots the total numbers of successful trials within the same day as obtained by the experiment for testing three algorithms: Kalman filtering; an algorithm as disclosed herein with online update; and the algorithm with fixed parameters.

FIG. 3A plots total numbers of successful trials within the same day as found in the experiment of running the rat lever-pressing task. The horizontal axis represents different days. The vertical axis shows the number of successful trials. The results of using the KF, the disclosed algorithm, and the disclosed algorithm with fixed parameters are shown in a left bar 310, a right bar 330, and a middle bar 320, respectively. The numbers of successful trials for KF are around two hundred trials according to the experimental paradigm. On day 1, since it was the first day of training, the successful trial numbers of all the three methods are similar. After day 1, the middle bar 320 is always higher than the left bar 310, exhibiting the advantage of the nonlinear observation-state mapping from the RL model. In FIG. 3A, the right bar 330 has the highest number of successful trials among the three bars 310, 320, 330, indicating that the disclosed algorithm is most effective in capturing non-stationary neural signals each day.

Figure 3B:
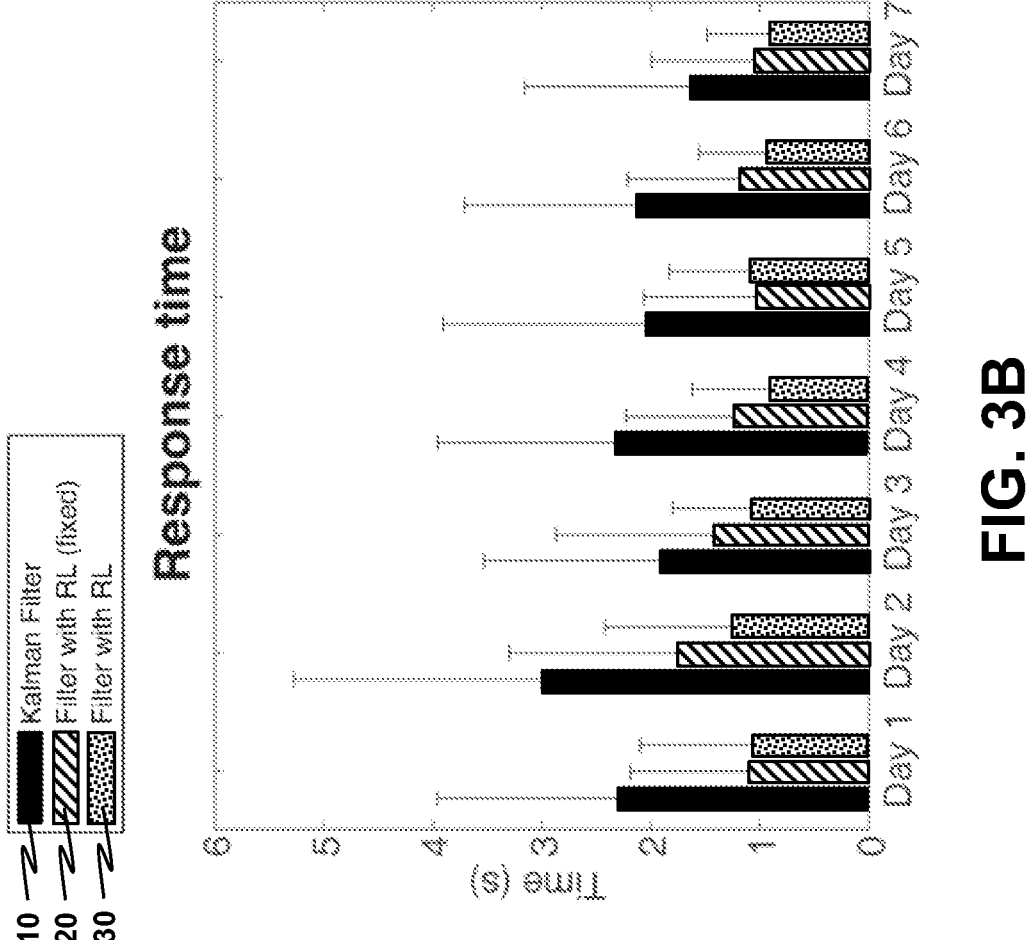
FIG. 3B plots the response times across different days as found in the experiment for the three algorithms.

FIG. 3B plots the response times across different days as found in the experiment. The response time is the time interval between the start cue and the success moment. A smaller response time means that the algorithm can finish the task more efficiently. The bar and the whisker represent the mean and standard deviation of the response time, respectively. The difference between the middle bar 320 and the left bar 310 shows the advantage of RL's nonlinear mapping from neural patterns to the state. The response time for KF and Filter with RL (fixed) has a large variance, illustrating that the neural patterns are non-stationary across days. For the disclosed algorithm with continuous update (the right bar 330), the response time is less than corresponding response times of the other two techniques. At the same time, the response time is more stable across days, showing that the disclosed algorithm with online update of RL successfully followed the change in the neural patterns.

Figure 3C:
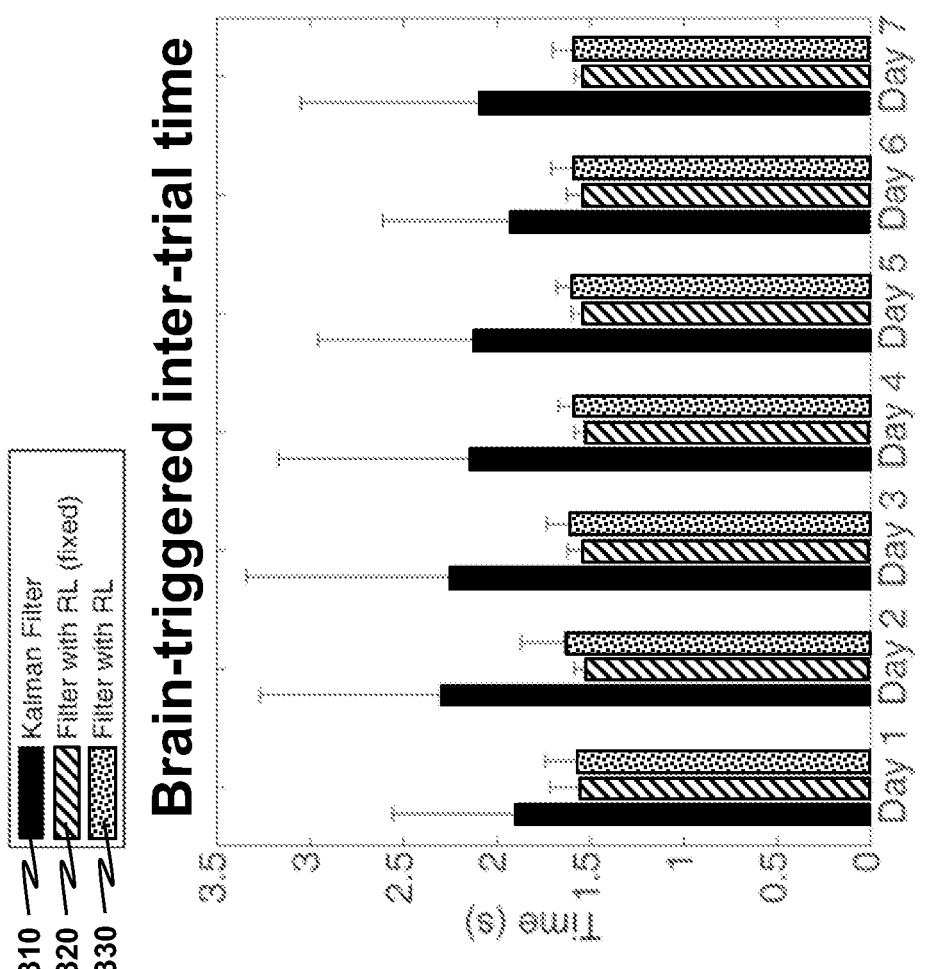
FIG. 3C plots the brain-triggered inter-trial times of the three algorithms as found in the experiment for the three algorithms.

FIG. 3C plots the brain-triggered inter-trial times of the three algorithms as found in the experiment. The brain-triggered inter-trial time is a time interval between the success time and the start cue of the next trial. A smaller brain-triggered inter-trial time implies that the algorithm could trigger the next trial faster, which is more likely to accomplish more trials within a given time. During the training process, the two disclosed algorithms (online update/fixed parameters) both have a smaller and more stable brain-triggered inter-trial time than the KF. The brain-triggered inter-trial time of online update and fixed parameters are similar, implying that the neural patterns between the success moment and the next trial start are relatively stable. The RL's nonlinear mapping trained from the first day is sufficient to drive the cursor from success to trigger the next start.

C. Details of Embodiments of the Present Invention

The present invention is developed based on the theoretical work and experimental verification as disclosed above.

Figure 4:
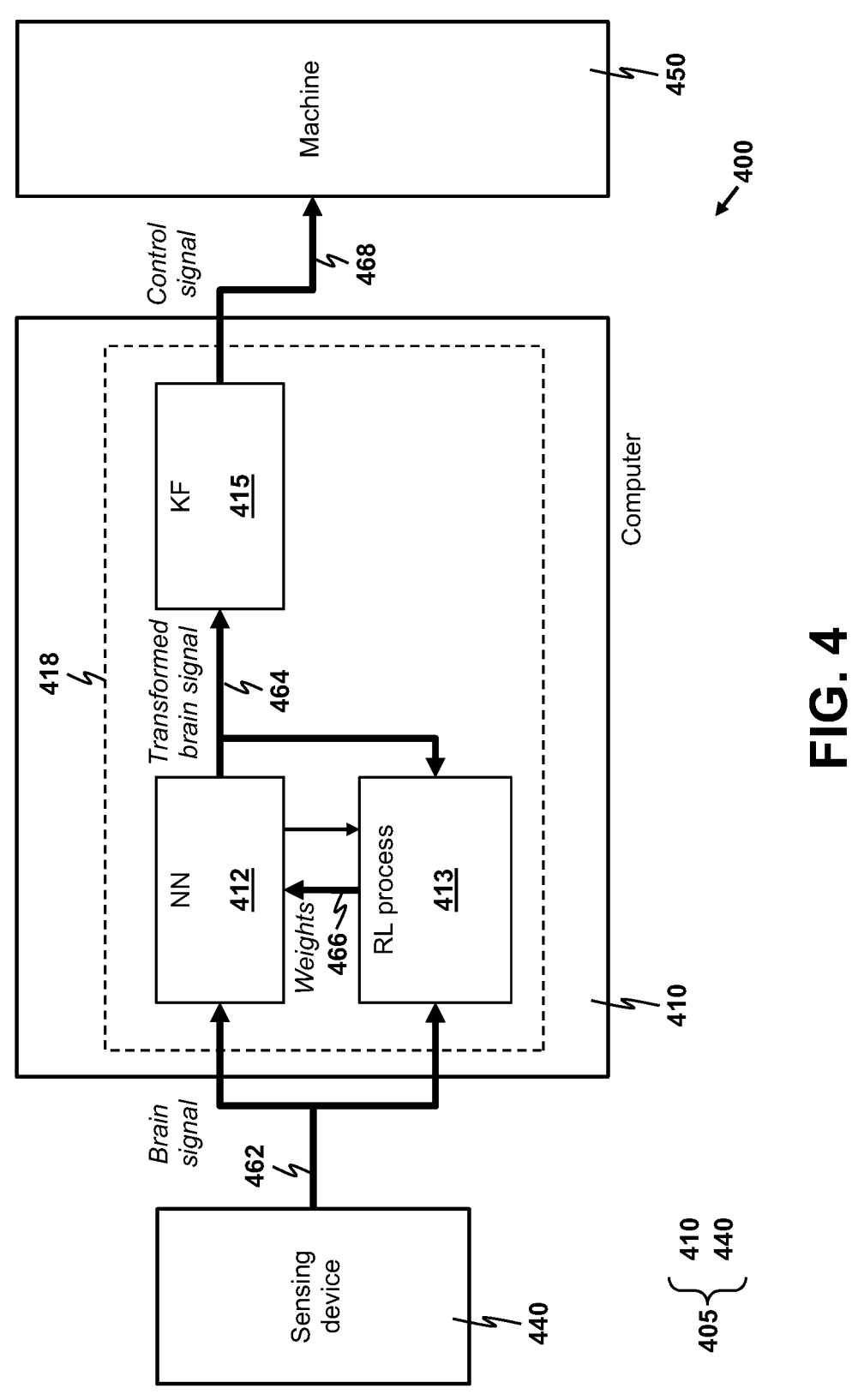
FIG. 4 is a schematic diagram of an exemplary system employing the disclosed RL-based adaptive state observation model for decoding a brain signal and subsequently performing a movement action as intended by the brain signal, where the model processes the brain signal with a NN followed by a KF, and a plurality of weights of the NN is updated by a RL process.

FIG. 4 depicts a schematic diagram of an exemplary system 400 that employs the RL-based adaptive state observation model as disclosed above for decoding a brain signal 462 of a subject to determine a movement action as intended by the subject, and that subsequently performs the movement action. A core part of the system 400 is a computer 410 configured with a RL-based adaptive state observation model 418 for decoding the brain signal 462, and generating a control signal 468 for controlling a machine 450 to perform the movement action. The system 400 acquires the brain signal 462 from the subject by using a sensing device 440 to sense the brain signal 462. In practical implementation, a BMI may be formed by the computer 410 alone, may be composed of the computer 410 and the sensing device 440, or may simply be a software item encoded with the RL-based adaptive state observation model 418.

A first aspect of the present invention is to provide a computer-implemented method for controlling the machine 450 to perform the movement action determined by the brain signal 462. The disclosed method is developed essentially according to the RL-based adaptive state observation model 418.

In the method, the brain signal 462 is processed by a NN 412 for applying a nonlinear mapping to the brain signal 462 to thereby yield a transformed brain signal 464. The nonlinear mapping is defined by a plurality of weights 466 of the NN 412. The plurality of weights 466 is updated by a RL process 413 such that the NN 412 learns the nonlinear mapping by RL. Note that the plurality of weights 466 is continuously updated over time as the brain signal 462 is continuously generated by the subject over time so that the brain signal 462 is a time series of signal samples, each sample being multidimensional. The plurality of weights 466 is updated once a new sample of the brain signal 462 is received. As a result of weight updating, it allows the nonlinear mapping provided by the NN 412 to be adaptively and continuously updated to follow nonlinearity and non-stationarity of the brain signal 462. The transformed brain signal 464, which is an output of the NN 412, is processed by a KF 415 to yield the control signal 468 used for controlling the machine to perform the movement action. The serial cascade of the NN 412 and the KF 415 advantageously utilizes the KF 415 to provide smooth generation of the control signal 468 while the NN 412 blocks the adverse influence of nonlinearity and non-stationarity of the brain signal 462 to the KF 415 in generating the control signal 468.

Figure 5:
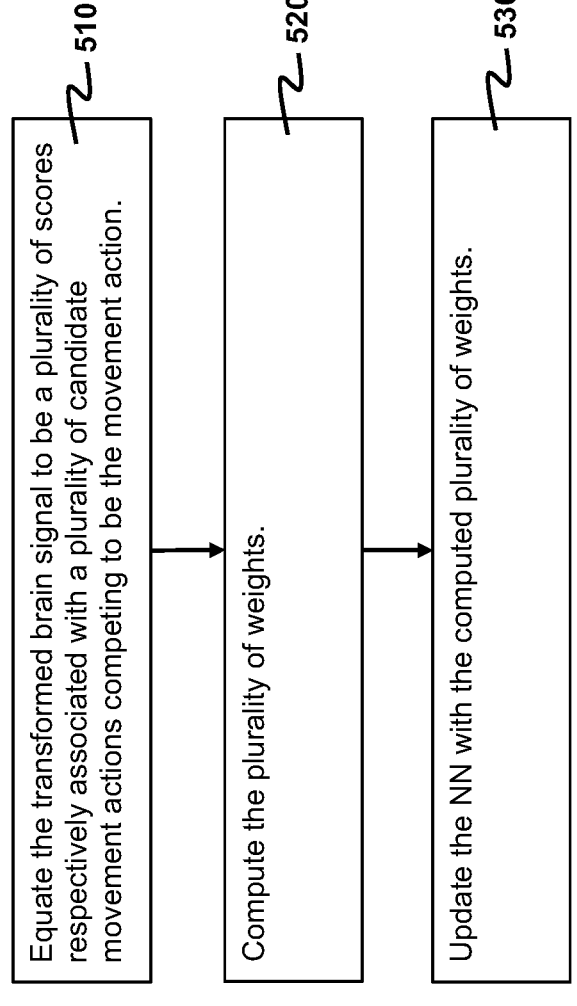
FIG. 5 depicts an exemplary embodiment of the RL process for updating the plurality of weights and thereby configuring a nonlinear mapping provided by the NN in processing the brain signal.

FIG. 5 depicts an exemplary embodiment of the RL process 413.

Note that the transformed brain signal 464, which serves one function of directing the KF 415 to generate the control signal 468, serves another function of being utilized by the RL process 413 to provide a feedback to the NN 412 through updating the plurality of weights 466. Also note that as mentioned above, the output layer of the NN 412 has plural nodes each representing a possible action. In this regard, consider that the movement action to be performed by the machine 450 is selected from plural candidate movement actions, and that the candidate movement actions compete to be the movement action.

In step 510, the RL process 413 equates the transformed brain signal 464 to be a plurality of scores respectively associated with a plurality of candidate movement actions competing to be the movement action. Specifically, an individual score of a respective candidate movement action is indicative to a probability that the respective candidate movement action is the movement action as intended by the brain signal 462. For illustration, the individual score corresponds to $y_k$, and the aforesaid probability corresponds to $P(\alpha_t = k')$ as shown in (10). The plurality of weights 466 is computed according to at least the plurality of scores in step 520. In step 530, the RL process 413 updates the NN 412 with the computed plurality of weight 466 for configuring the nonlinear mapping.

It is believed that the brain signal 462 and the plurality of scores each indicative to a probability that a certain candidate movement action is the movement action are two signals of different nature and, therefore, the two signals have vastly different statistical behaviors. By treating the transformed brain signal 464 as the plurality of scores in the RL process 413, and noting that the transformed brain signal 464 is obtained at the output of the NN 412, it is believed that updating the NN 412 with the plurality of weights 466 computed according to the plurality of scores potentially drives the NN 412 to somehow "absorb" nonlinearity and non-stationarity of the incoming brain signal 462 in order to generate the plurality of scores at the output of the NN 412. Furthermore, treating the transformed brain signal 464 as the plurality of scores enables RL to be applicable to the NN 412. It follows that the equating of the transformed brain signal 464 to be the plurality of scores in computing the plurality of weights 466 and updating the NN 412 with the computed plurality of weights 466 guides the nonlinear mapping to follow nonlinearity and non-stationarity of the brain signal 462 as well as allows RL to be applied to NN learning.

FIG. 6 depicts certain embodiments of step 520.

In step 610, a plurality of probabilities associated with the plurality of candidate movement actions is computed from the plurality of scores. As used herein, the plurality of probabilities associated with the plurality of candidate movement actions is understood as follows: an individual probability associated with a respective candidate movement action is the probability that the respective candidate movement action is the movement action as intended by the brain signal 462. In certain embodiments, $P(\alpha_t = k')$, the probability that a k'th candidate movement action in the plurality of candidate movement actions is the movement action as intended by the brain signal 462, is computed by (10), where N is a total number of candidate movement actions in the plurality of candidate movement actions, $y_t = [y_1, \ldots, y_N]^T$ is the transformed brain signal 464 with $y_k$ being a kth component of $y_t$, and $\alpha \geq 0$ is a controlling parameter.

In step 620, one candidate movement action is selected from the plurality of candidate movement actions as a winner in competing to be the movement action as intended. The selection is made according to the plurality of probabilities as computed in step 610. In certain embodiments, the winner is selected to be a k*th candidate movement action such that $P(\alpha_t=k^*)$ is greatest among all N values of $P(\alpha_t=k')$, k'=1, . . . , N.

After step 620 is accomplished, a reward due to selecting the winner as the movement action is determined in step 630. In particular, the reward is determined according to whether or not the winner is actually the movement action as intended. In certain embodiments, $r_t$, the reward due to selecting the k*th candidate movement action as the movement action, is given by $r_t=1$ if the the k*th candidate movement action is the movement action as intended by the brain signal, and $r_t=0$ if not In step 640, the plurality of weights 466 is computed according to at least the reward determined in step 630. In accordance with certain embodiments, the computation of the plurality of weights 466 under a specific case that the NN 412 is a three-layer NN is elaborated as follows. The three-layer NN has an input layer, an output layer, and a hidden layer between the input and output layers. The input layer has $D_z$ nodes for receiving the brain signal 462. Note that the brain signal 462 has $D_z$ components in one signal sample obtained at a time instant. The hidden layer has J hidden units. The output layer has N nodes for outputting the transformed brain signal 464. Hence, the transformed brain signal 464 has N components in one signal sample obtained at a time instant. The plurality of weights 466, which is composed of $\{w_{ij}|i=1, . . . , D_z; j=1, . . . , J\}$ and $\{v_{jk}|j=1, . . . , J; k=1, . . . , N\}$, is computed by (13) and (14), where: $w_{ij}$ is a weight from an ith node of the input layer to a jth hidden unit; $v_{jk*}$ is a weight from the jth hidden unit to a k*th node of the output layer, k* being an index used to indicate that a k*th candidate movement action is selected from the N candidate movement actions as the winner in competing to be the movement action as intended by the brain signal 462; $\gamma$ is a learning rate; $\delta$ is an error function computed by (11); $f(\delta)$ is an error expansive function given by (12); $z_{ti}$ is an ith component of $z_t$, the brain signal 462 obtained at time step t; and $h_j$ is a value of the jth hidden unit, given by (8).

Refer to FIG. 4. The control signal 468 is generated by the KF 415 based on $y_t$, a signal sample of the transformed brain signal 464 obtained at time step t. Exemplarily, the control signal 468 is computed as $x_{t|t}$ given by $$x_{t|t}=x_{t|t-1}+K(y_t-x_{t|t-1}) \quad (20)$$

where: $x_{t|t}$ is a posterior estimation of a mean of a state x at time step t; $x_{t|t-1}$ is a prior estimation of the mean of the state x at time step t; and K is a Kalman gain given by (16), in which $P_{t|t}$ is a posterior estimation of the covariance of the state x at time step t, and R is a covariance matrix of a Gaussian noise term in $y_t$. Note that the state x is a state of the KF 415. Furthermore, the KF 415 is used to model the machine 450. Hence, the state transition matrix F may be formulated according to characteristics of the machine 450.

A second aspect of the present invention is to provide the system 400 for capturing the brain signal 462 of the subject and performing a movement action determined by the brain signal 462.

The system 400 comprises the sensing device 440 for capturing the brain signal 462 from the subject, the machine 450 for performing the movement action, and the computer 410 configured to execute a computing process of processing the brain signal 462 to determine the movement action and controlling the machine 450 to perform the movement action. Particularly, the computing process is realized as any of the embodiments of the method disclosed above under the first aspect of the present invention.

Note that the computer 410 is further configured to receive the brain signal 462 from the sensing device 440. The computer 410 may be connected, wirelessly or through wirelines, to the sensing device 440.

The sensing device 440 may be an EEG sensing device, a fMRI device, etc. The sensing device 440 may even be a plurality of electrodes implanted in the brain of the subject (if, for example, the subject has a serious, irrecoverable spinal-cord injury).

The machine 450 may be a prosthesis, or a second computer configured to generate the movement action on a virtual object for virtual-reality applications.

A third aspect of the present invention is to provide a BMI apparatus 405 for capturing the brain signal 462 of the subject and controlling the machine 450 to perform a movement action determined by the brain signal 462.

The BMI apparatus 405 comprises the sensing device 440 for capturing the brain signal 462 from the subject, and the computer 410 configured to execute a computing process of processing the brain signal 462 to determine the movement action and controlling the machine 450 to perform the movement action. The computing process is realized as any of the embodiments of the method disclosed above under the first aspect of the present invention.

Note that the computer 410 is further configured to receive the brain signal 462 from the sensing device 440. The computer 410 may be connected, wirelessly or through wirelines, to the sensing device 440.

The sensing device 440 may be an EEG sensing device, a fMRI device, etc.

The present disclosure may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A computer-implemented method for controlling a machine to perform a movement action determined by a brain signal of a subject, the method comprising:
   processing the brain signal with a neural network (NN) for applying a nonlinear mapping defined by a plurality of weights of the NN to the brain signal to thereby yield a transformed brain signal;
   updating the plurality of weights by a reinforcement learning (RL) process such that the NN learns the nonlinear mapping by RL; and
   processing the transformed brain signal with a Kalman filter (KF) to yield a control signal for controlling the machine to perform the movement action, wherein the control signal is computed as $x_{t|t}$ given by $$x_{t|t}=x_{t|t-1}+K(y_t-x_{t|t-1})$$

where:
   $x_{t|t}$ is a posterior estimation of a mean of a state x at time step t, wherein the state x is a state of the KF, the KF being used to model the machine;
   $x_{t|t-1}$ is a prior estimation of the mean of the state x at time step t; and
   K is a Kalman gain given by $K=P_{t|t-1}(P_{t|t-1}+R)^{-1}$ where is a prior estimation of the covariance of the state x at time step t, and R is a covariance matrix of a Gaussian noise term in $y_t$, in which $y_t$ is the transformed brain signal generated by the NN at time step t.

2. The method of claim 1, wherein the RL process comprises:

equating the transformed brain signal to be a plurality of scores respectively associated with a plurality of candidate movement actions competing to be the movement action, an individual score of a respective candidate movement action being indicative to a probability that the respective candidate movement action is the movement action;

computing the plurality of weights according to at least the plurality of scores; and updating the NN with the computed plurality of weights for configuring the nonlinear mapping.

3. The method of claim 2, wherein the computing of the plurality of weights according to at least the plurality of scores comprises:

computing, from the plurality of scores, a plurality of probabilities associated with the plurality of candidate movement actions, wherein an individual probability associated with the respective candidate movement action is the probability that the respective candidate movement action is the movement action;

selecting, from the plurality of candidate movement actions, a winner in competing to be the movement action according to the plurality of probabilities;

determining a reward due to selecting the winner as the movement action according to whether or not the winner is the movement action; and computing the plurality of weights according to at least the reward.

4. The method of claim 3, wherein:

$P(a_t=k')$, the probability that a k'th candidate movement action in the plurality of candidate movement actions is the movement action, is computed by $$P(a_t = k') = \frac{\exp(\alpha y_{k'})}{\sum_{k=1}^{N} \exp(\alpha y_k)}$$

where N is a total number of candidate movement actions in the plurality of candidate movement actions, $y_t=[y_1, \ldots, y_N]^T$ is the transformed brain signal with $y_k$ being a kth component of $y_t$, and $\alpha \geq 0$ is a controlling parameter; and the winner is selected to be a k*th candidate movement action from $P(a_t=k^*)$ among all N probability values of $P(a_t=k')$, k'=1, . . . , N.

5. The method of claim 4, wherein $r_t$, the reward due to selecting the k*th candidate movement action as the movement action, is given by $r_t=1$ if the k*th candidate movement action is the movement action, and $r_t=0$ if not.

6. The method of claim 5, wherein:

the NN is a three-layer NN comprising:

an input layer having $D_z$ nodes for receiving the brain signal, the brain signal having $D_z$ components;

a hidden layer having J hidden units; and an output layer having N nodes for outputting the transformed brain signal, the transformed brain signal having N components; and the plurality of weights is computed by $$v_{jk}^* \leftarrow v_{jk}^* + \gamma h_j f(\delta), j=1, \ldots, J,$$

and $$w_{ij} \leftarrow w_{ij} + \gamma z_{ti} h_j f(\delta) v_{jk^*}(1-h_j), i=1, \ldots, D_z \text{ and } j=1, \ldots, J,$$

where:

$w_{ij}$ is a weight from an ith node of the input layer to a jth hidden unit;

$v_{jk^*}$ is a weight from the jth hidden unit to a k*th node of the output layer;

'$\leftarrow$' is an assignment operator meaning that the variable at the left hand side of the operator is assigned with a value computed by the expression shown on the right hand side of the operator;

$\gamma$ is a learning rate;

$\delta$ is an error function computed by $\delta = r_t - P(a_t=k^*)$;

$f(\delta)$ is an error expansive function given by $$f(\delta) = \begin{cases} \dfrac{\delta}{1-\delta}, & \delta \geq 0, \\ -1, & \delta < 0; \end{cases}$$

$z_{ti}$ is an ith component of $z_t$, the brain signal obtained at time step t; and $h_j$ is a value of the jth hidden unit, given by $$h_j = \frac{1}{1 + \exp\left(-\sum_{i=1}^{D_z} w_{ij} z_{ti}\right)}.$$

7. A system for capturing a brain signal of a subject and performing a movement action determined by the brain signal, the system comprising:

a sensing device for capturing the brain signal from the subject;

a machine for performing the movement action; and a computer configured to execute a computing process of processing the brain signal to determine the movement action and controlling the machine to perform the movement action according to the method of claim 1.

8. The system of claim 7, wherein the sensing device is an electroencephalogram (EEG) sensing device.

9. The system of claim 7, wherein the machine is a prosthesis.

10. The system of claim 7, wherein the machine is a second computer configured to generate the movement action on a virtual object for virtual-reality applications.

11. A brain-machine interface (BMI) apparatus for capturing a brain signal of a subject and controlling a machine to perform a movement action determined by the brain signal, the BMI apparatus comprising:

a sensing device for capturing the brain signal from the subject; and a computer configured to execute a computing process of processing the brain signal to determine the movement action and controlling the machine to perform the movement action according to the method of claim 1.

12. The BMI apparatus of claim 11, wherein the sensing device is an electroencephalogram (EEG) sensing device.

13. A computer-implemented method for controlling a machine to perform a movement action determined by a brain signal of a subject, the method comprising:

processing the brain signal with a neural network (NN) for applying a nonlinear mapping defined by a plurality of weights of the NN to the brain signal to thereby yield a transformed brain signal;

updating the plurality of weights by a reinforcement learning (RL) process such that the NN learns the nonlinear mapping by RL; and

processing the transformed brain signal with a Kalman filter (KF) to yield a control signal for controlling the machine to perform the movement action;

wherein the RL process comprises:

equating the transformed brain signal to be a plurality of scores respectively associated with a plurality of candidate movement actions competing to be the movement action, an individual score of a respective candidate movement action being indicative to a probability that the respective candidate movement action is the movement action;

computing the plurality of weights according to at least the plurality of scores; and updating the NN with the computed plurality of weights for configuring the nonlinear mapping;

wherein the computing of the plurality of weights according to at least the plurality of scores comprises:

computing, from the plurality of scores, a plurality of probabilities associated with the plurality of candidate movement actions, wherein an individual probability associated with the respective candidate movement action is the probability that the respective candidate movement action is the movement action;

selecting, from the plurality of candidate movement actions, a winner in competing to be the movement action according to the plurality of probabilities;

determining a reward due to selecting the winner as the movement action according to whether or not the winner is the movement action; and computing the plurality of weights according to at least the reward;

wherein $P(a_t=k')$, the probability that a k'th candidate movement action in the plurality of candidate movement actions is the movement action, is computed by $$P(a_t = k') = \frac{\exp(\alpha y'_k)}{\sum_{k=1}^{N} \exp(\alpha y_k)}$$

where N is a total number of candidate movement actions in the plurality of candidate movement actions, $y_t=[y_1, \ldots, y_N]^T$ is the transformed brain signal with $y_k$ being a kth component of $y_t$, and $\alpha \geq 0$ is a controlling parameter; and wherein the winner is selected to be a k*th candidate movement action from $P(a_t=k*)$ among all N probability values of $P(a_t=k')$, $k'=1, \ldots, N$.

14. The method of claim 13, wherein $r_t$, the reward due to selecting the k*th candidate movement action as the movement action, is given by $r_t=1$ if the k*th candidate movement action is the movement action, and $r_t=0$ if not.

15. The method of claim 14, wherein:

the NN is a three-layer NN comprising:

an input layer having $D_z$ nodes for receiving the brain signal, the brain signal having $D_z$ components;

a hidden layer having/hidden units; and an output layer having N nodes for outputting the transformed brain signal, the transformed brain signal having N components; and

the plurality of weights is computed by $$v_{jk}* \leftarrow v_{jk}*+\gamma h_j f(\delta), j=1, \ldots, J,$$

and $$w_{ij} \leftarrow w_{ij}+\gamma z_{ti} h_j f(\delta) v_{jk*}(1-h_j), i=1, \ldots, D_z$$
and $j=1, \ldots, J,$ where:

$w_{ij}$ is a weight from an ith node of the input layer to a jth hidden unit;

$v_{jk*}$ is a weight from the jth hidden unit to a k*th node of the output layer;

'←' is an assignment operator meaning that the variable at the left hand side of the operator is assigned with a value computed by the expression shown on the right hand side of the operator;

$\gamma$ is a learning rate;

$\delta$ is an error function computed by $\delta=r_t-P(a_t=k*)$;

$f(\delta)$ is an error expansive function given by $$f(\delta) = \begin{cases} \dfrac{\delta}{1-\delta}, & \delta \geq 0, \\ -1, & \delta < 0; \end{cases}$$

$z_{ti}$ is an ith component of $z_t$, the brain signal obtained at time step t; and $h_j$ is a value of the jth hidden unit, given by $$h_j = \frac{1}{1 + \exp\left(-\sum_{i=1}^{D_z} w_{ij} z_{ti}\right)}.$$

16. A system for capturing a brain signal of a subject and performing a movement action determined by the brain signal, the system comprising:

a sensing device for capturing the brain signal from the subject;

a machine for performing the movement action; and a computer configured to execute a computing process of processing the brain signal to determine the movement action and controlling the machine to perform the movement action according to the method of claim 13.

17. The system of claim 16, wherein the sensing device is an electroencephalogram (EEG) sensing device.

18. The system of claim 16, wherein the machine is a prosthesis.

19. The system of claim 16, wherein the machine is a second computer configured to generate the movement action on a virtual object for virtual-reality applications.

20. A brain-machine interface (BMI) apparatus for capturing a brain signal of a subject and controlling a machine to perform a movement action determined by the brain signal, the BMI apparatus comprising:

a sensing device for capturing the brain signal from the subject; and a computer configured to execute a computing process of processing the brain signal to determine the movement action and controlling the machine to perform the movement action according to the method of claim 13.

* * * * *